US 6,564,390 B2

(12) United States Patent
Vernon

(10) Patent No.: US 6,564,390 B2
(45) Date of Patent: May 20, 2003

(54) ABSORBENT HEADBAND APPARATUS

(76) Inventor: Amelia Rose Vernon, 251 W. Faculty Ave., Paoli, IN (US) 47454

( * ) Notice: Subject to any disclaimer, the term of this patent is extended or adjusted under 35 U.S.C. 154(b) by 0 days.

(21) Appl. No.: 10/053,361
(22) Filed: Jan. 17, 2002

(65) Prior Publication Data
US 2002/0095714 A1 Jul. 25, 2002

Related U.S. Application Data
(60) Provisional application No. 60/264,197, filed on Jan. 25, 2001.

(51) Int. Cl.$^7$ .................................................. A42B 1/00
(52) U.S. Cl. ........................................ 2/171; 2/181
(58) Field of Search ................... 2/410, 425, 171, 2/181, 181.6, 182.3, DIG. 11, 918, 174

(56) References Cited

U.S. PATENT DOCUMENTS

| | | | |
|---|---|---|---|
| 2,016,210 A | * 10/1935 | Mann | 2/171 |
| 2,783,474 A | * 3/1957 | Campagna et al. | 2/171 |
| 4,502,156 A | * 3/1985 | Wishman | 2/171.2 |
| 4,856,116 A | 8/1989 | Sullivan | |
| 5,105,476 A | * 4/1992 | Cox | 2/12 |
| 5,146,630 A | 9/1992 | Richard | |
| 5,175,887 A | * 1/1993 | Kim | 2/174 |
| 5,377,360 A | * 1/1995 | Fleitman | 2/171 |
| 5,802,865 A | * 9/1998 | Strauss | 62/259.3 |
| 5,826,277 A | 10/1998 | McConville | |
| 5,915,532 A | * 6/1999 | Williams | 2/171 |
| 5,946,734 A | 9/1999 | Vogan | |
| 5,987,647 A | 11/1999 | Ouellette | |

* cited by examiner

Primary Examiner—Gary L. Welch

(57) ABSTRACT

A headband apparatus includes a flexible, resilient C-shaped core member. A first absorbent layer is attached to the core member. A cloth layer is attached to the first absorbent layer, and a second absorbent layer is attached to an inside portion of the first absorbent layer under the cloth layer. The first absorbent layer jackets the core member. The core member is comprised of a flexible, resilient plastic material. The first absorbent layer is comprised of foam first material. The cloth layer jackets the first absorbent layer. The cloth layer is comprised of terrycloth material. The second absorbent layer is comprised of loose foam second material. When the midportion of the apparatus is placed on the forehead of a person, the first absorbent layer, the cloth layer, and the second absorbent layer are all capable of absorbing perspiration from the person's forehead.

8 Claims, 3 Drawing Sheets

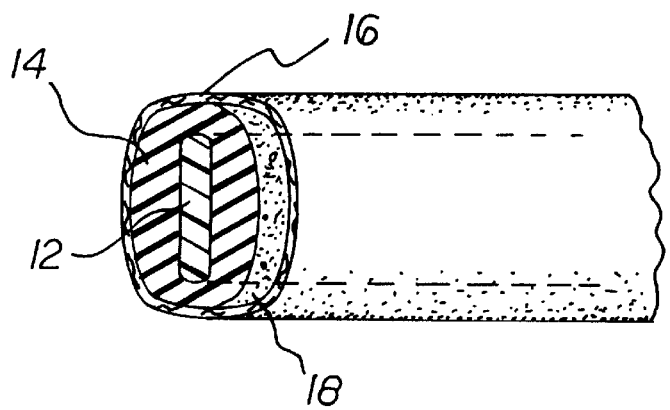
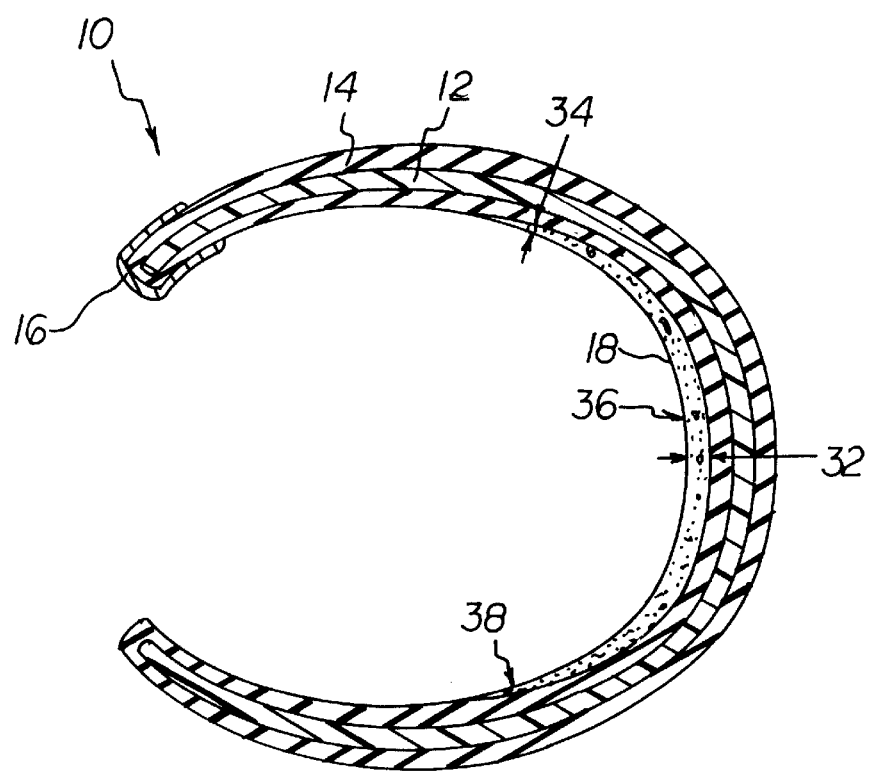

ABSORBENT HEADBAND APPARATUS

CROSS-REFERENCE TO RELATED APPLICATION

This application claims priority based upon my copending Provisional Application Serial No. 60/264,197; filed Jan. 25, 2001.

BACKGROUND OF THE INVENTION

1. Field of the Invention

The present invention relates generally to headbands and, more particularly, to headbands especially adapted for absorbing perspiration from a person's forehead.

2. Description of the Prior Art

When perspiration forms on a person's forehead, it often flow downward into the person's eyes and/or onto the person's eyeglasses. To avoid this undesirable result, throughout the years, a number of innovations have been developed relating to headbands, and the following U.S. patents are representative of some of those innovations: U.S. Pat. Nos. 4,856,116, 5,146,630, 5,826,277, 5,946,734, and 5,987,647. More specifically, U.S. Pat. Nos. 4,856,116 and 5,987,647 disclose headbands in which an absorbent core is provided with a covering. In U.S. Pat. No. 4,856,116, there is no tapering either from midportion height to end portion height or from midportion thickness to end portion thickness. In U.S. Pat. No. 5,987,647 there is a tapering from midportion height to end portion height, but there is no tapering from midportion thickness to end portion thickness. Thus, in both U.S. Pat. Nos. 4,856,116 and 5,987,647, there is no tapering from midportion thickness to end portion thickness. Because most perspiration forms at the midportion position, and lesser amounts of perspiration form at the end portion positions, it would be desirable if a headband apparatus were provided in which the midportion thickness were greater than the end portion thickness.

U.S. Pat. No. 5,146,630 discloses a headband in which a removable package containing granular moisture absorbent material is provided. To avoid the necessity of employing extraneous packages of granular perspiration absorbent material, it would be desirable if a headband were provided which does not include packages of granular perspiration absorbent material.

U.S. Pat. No. 5,826,277 discloses a headband which includes an elastic band and inelastic sponge material sewn onto the elastic band at predetermined alternating intervals. At the sewn seam locations, a minimum exposure of the inelastic sponge material is provided. To avoid a situation in which a minimum exposure of absorbent material is alternated with maximum exposure of absorbent material, it would be desirable if a headband were provided which does not include inelastic sponge material sewn onto an elastic band at alternating intervals.

U.S. Pat. No. 5,946,734 discloses a headband which includes rupturable, pressurized, fluid filled cells that provide impact protection to a person wearing the headband. However, the material comprising the rupturable, pressurized, fluid filled cells is inherently not perspiration absorbent. Thus, to maintain the desirable property of having a headband being perspiration absorbent, it would be desirable if a headband does not include rupturable, pressurized, fluid filled cells.

Still other features would be desirable in an absorbent headband apparatus. For example, it would be desirable to provide an specific absorbent layer, which is closest to the wearer's forehead, in which a midportion layer thickness is greater than the thickness at the ends of the specific absorbent layer. In this respect, the specific layer midportion tapers to the specific layer end portions.

Another desirable feature in a headband is to have the midportion height greater than the end portion height. In this respect, the present invention provides a headband in which the midportion height is greater than the end portion height.

Thus, while the foregoing body of prior art indicates it to be well known to use headbands that absorb perspiration from a wearer's forehead, the prior art described above does not teach or suggest an absorbent headband apparatus which has the following combination of desirable features: (1) the midportion thickness is greater than the end portion thickness; (2) does not include packages of granular perspiration absorbent material; (3) does not include inelastic sponge material sewn onto an elastic band at alternating intervals; (4) does not include rupturable, pressurized, fluid filled cells; (5) provides a specific absorbent layer, which is closest to the wearer's forehead, in which a midportion layer thickness is greater than the thickness at the ends of the specific absorbent layer; and (6) the midportion height is greater than the end portion height. The foregoing desired characteristics are provided by the unique absorbent headband apparatus of the present invention as will be made apparent from the following description thereof. Other advantages of the present invention over the prior art also will be rendered evident.

SUMMARY OF THE INVENTION

To achieve the foregoing and other advantages, the present invention, briefly described, provides a headband apparatus which includes a flexible, resilient C-shaped core member. A first absorbent layer is attached to the core member. A cloth layer is attached to the first absorbent layer, and a second absorbent layer is attached to an inside portion of the first absorbent layer under the cloth layer. The first absorbent layer jackets the core member. The core member is comprised of a flexible, resilient plastic material. The first absorbent layer is comprised of foam first material. The cloth layer jackets the first absorbent layer. The cloth layer is comprised of terrycloth material. The second absorbent layer is comprised of loose foam second material. When the midportion of the apparatus is placed on the forehead of a person, the first absorbent layer, the cloth layer, and the second absorbent layer are all capable of absorbing perspiration from the person's forehead.

The apparatus has a midportion and two end portions. The midportion has a midportion thickness. Each of the two end portions has an end portion thickness, and the midportion thickness is greater than the end portion thickness, whereby the thickness of the apparatus tapers from the midportion to the two end portions. Also, the midportion has a midportion height. Each of the two end portions has an end portion height, and the midportion height is greater than the end portion height, whereby the height of the apparatus tapers from the midportion to the two end portions.

The second absorbent layer includes a layer midportion which has a midportion layer thickness and includes two layer end portions which have an end layer thickness. The midportion layer thickness is greater than the end layer thickness, whereby the thickness of the second absorbent layer tapers from the layer midportion to the layer end portions.

The above brief description sets forth rather broadly the more important features of the present invention in order that the detailed description thereof that follows may be better understood, and in order that the present contributions to the art may be better appreciated. There are, of course, additional features of the invention that will be described hereinafter and which will be for the subject matter of the claims appended hereto.

In this respect, before explaining a preferred embodiment of the invention in detail, it is understood that the invention is not limited in its application to the details of the construction and to the arrangements of the components set forth in the following description or illustrated in the drawings. The invention is capable of other embodiments and of being practiced and carried out in various ways. Also, it is to be understood, that the phraseology and terminology employed herein are for the purpose of description and should not be regarded as limiting.

As such, those skilled in the art will appreciate that the conception, upon which disclosure is based, may readily be utilized as a basis for designing other structures, methods, and systems for carrying out the several purposes of the present invention. It is important, therefore, that the claims be regarded as including such equivalent constructions insofar as they do not depart from the spirit and scope of the present invention.

It is therefore an object of the present invention to provide a new and improved absorbent headband apparatus which has all of the advantages of the prior art and none of the disadvantages.

It is another object of the present invention to provide a new and improved absorbent headband apparatus which may be easily and efficiently manufactured and marketed.

It is a further object of the present invention to provide a new and improved absorbent headband apparatus which is of durable and reliable construction.

An even further object of the present invention is to provide a new and improved absorbent headband apparatus which is susceptible of a low cost of manufacture with regard to both materials and labor, and which accordingly is then susceptible of low prices of sale to the consuming public, thereby making such absorbent headband apparatus available to the buying public.

Still yet a further object of the present invention is to provide a new and improved absorbent headband apparatus in which the midportion thickness is greater than the end portion thickness.

Still another object of the present invention is to provide a new and improved absorbent headband apparatus that does not include packages of granular perspiration absorbent material.

Yet another object of the present invention is to provide a new and improved absorbent headband apparatus which does not include inelastic sponge material sewn onto an elastic band at alternating intervals.

Even another object of the present invention is to provide a new and improved absorbent headband apparatus that does not include rupturable, pressurized, fluid filled cells.

Still a further object of the present invention is to provide a new and improved absorbent headband apparatus which provides a specific absorbent layer, which is closest to the wearer's forehead, in which a midportion layer thickness is greater than the thickness at the ends of the specific absorbent layer.

Yet another object of the present invention is to provide a new and improved absorbent headband apparatus in which the midportion height is greater than the end portion height.

These together with still other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there are illustrated preferred embodiments of the invention.

BRIEF DESCRIPTION OF THE DRAWINGS

The invention will be better understood and the above objects as well as objects other than those set forth above will become more apparent after a study of the following detailed description thereof. Such description makes reference to the annexed drawing wherein:

FIG. 5 is cross-sectional view of the embodiment of the invention shown in FIG. 3 taken along line 5—5 thereof.

FIG. 6 is a cross-sectional view of the embodiment of the invention shown in FIG. 4 taken along line 6—6 thereof.

DESCRIPTION OF THE PREFERRED EMBODIMENT

With reference to the drawings, a new and improved absorbent headband apparatus embodying the principles and concepts of the present invention will be described.

Figure 1:
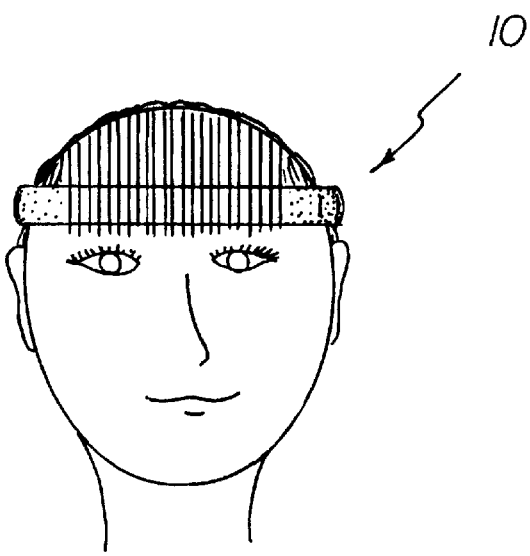
FIG. 1 is a front view showing a preferred embodiment of the absorbent headband apparatus of the invention being worn by a person.
Figure 2:
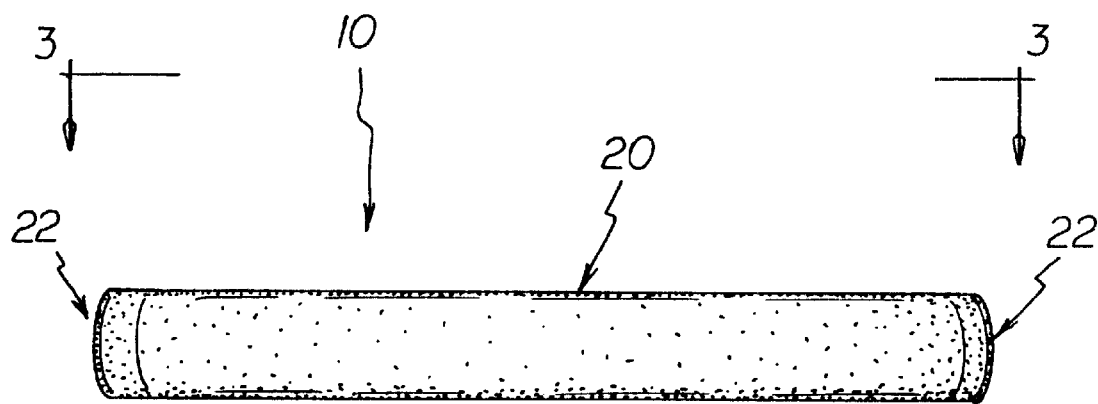
FIG. 2 is an enlarged rear view of the embodiment of the absorbent headband apparatus shown in FIG. 1 removed from the person.
Figure 3:
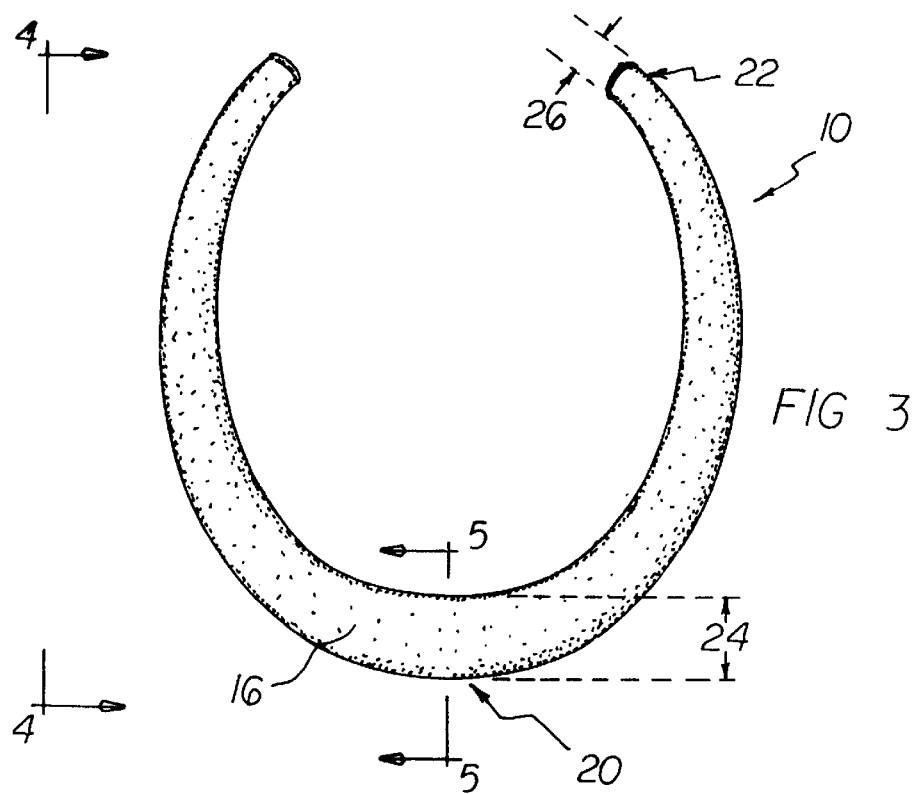
FIG. 3 is a top view of the embodiment of the absorbent headband apparatus of FIG. 2 taken along line 3—3 thereof.
Figure 4:
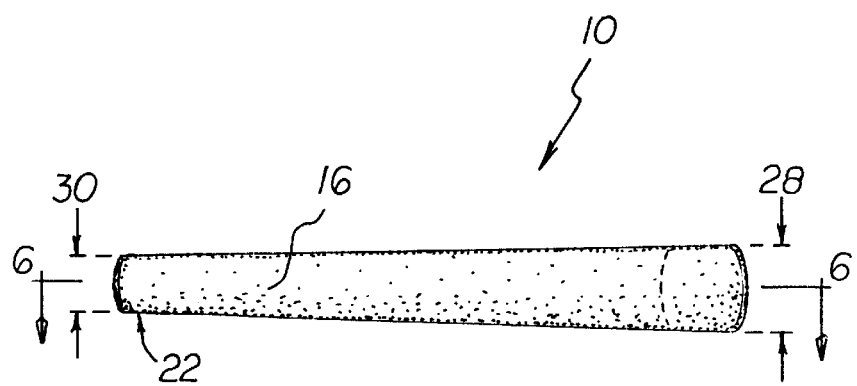
FIG. 4 is a side view of the embodiment of the invention shown in FIG. 3 taken along line 4—4 thereof.

Turning to FIGS. 1–6, there is shown an exemplary embodiment of the absorbent headband apparatus of the invention generally designated by reference numeral 10. In its preferred form, absorbent headband apparatus 10 includes a flexible, resilient C-shaped core member 12. A first absorbent layer 14 is attached to the core member 12. A cloth layer 16 is attached to the first absorbent layer 14, and a second absorbent layer 18 is attached to an inside portion of the first absorbent layer 14 under the cloth layer 16. The first absorbent layer 14 jackets the core member 12. The core member 12 is comprised of a flexible, resilient plastic material. The first absorbent layer 14 is comprised of foam first material. The cloth layer 16 jackets the first absorbent layer 14. In FIG. 6, the cloth layer 16 is shown extending about the end of headband apparatus 10 merely to avoid confusing this drawing. It will be appreciated that the cloth layer 16 extends about the entire apparatus 10 substantially as shown in FIGS. 2, 3 and 4. The cloth layer 16 is comprised of terrycloth material. The terrycloth material can be of a wide variety of descriptions and designs. The second absorbent layer 18 is comprised of loose foam second material. When the midportion 20 of the apparatus is placed on the forehead of a person, the first absorbent layer 14, the cloth layer 16, and the second absorbent layer 18 are all capable of absorbing perspiration from the person's forehead.

The apparatus has a midportion 20 and two end portions 22. The midportion 20 has a midportion thickness 24. Each of the two end portions 22 has an end portion thickness 26, and the midportion thickness 24 is greater than the end portion thickness 26, whereby the thickness of the apparatus tapers from the midportion 20 to the two end portions 22. Also, the midportion 20 has a midportion height 28. Each of the two end portions 22 has an end portion height 30, and the midportion height 28 is greater than the end portion height 30, whereby the height of the apparatus tapers from the midportion 20 to the two end portions 22.

The second absorbent layer 18 includes a layer midportion 36 which has a midportion layer thickness 32 and includes two layer end portions 38 which have an end layer thickness 34. The midportion layer thickness 32 is greater than the end layer thickness 34, whereby the thickness of the second absorbent layer 18 tapers from the layer midportion 36 to the layer end portions 38.

To use the headband apparatus 10 of the invention, the midportion 20 of the apparatus is placed on the center of a person's forehead, as shown in FIG. 1. When this is done, the end portions 22 of the apparatus contact temple portions of the person's head. Then, perspiration from the person's forehead is absorbed by the apparatus. As shown in FIG. 1. A portion of the person's hair, such as the bangs, can be combed over the apparatus when worn by the person.

The headband apparatus 10 of the invention can be worn as a sweatband to soak up a person's perspiration to prevent the perspiration from flowing into the person's eyes. At the same time the apparatus is worn to soak up perspiration, the apparatus serves as a fashionable head garment. Alternatively, the apparatus can be worn as a fashionable head garment for appearance improvement only. The headband apparatus 10 of the invention can be called a "Jmelie". The apparatus can be used by both men and women. There can be a "his" model and a "hers" model.

The components of the absorbent headband apparatus of the invention can be made from inexpensive and durable metal, cloth, and plastic materials.

As to the manner of usage and operation of the instant invention, the same is apparent from the above disclosure, and accordingly, no further discussion relative to the manner of usage and operation need be provided.

It is apparent from the above that the present invention accomplishes all of the objects set forth by providing a new and improved absorbent headband apparatus that is low in cost, relatively simple in design and operation, and which advantageously has a midportion thickness which is greater than the end portion thickness. With the invention, an absorbent headband apparatus is provided which does not include packages of granular perspiration absorbent material. With the invention, an absorbent headband apparatus is provided which does not include inelastic sponge material sewn onto an elastic band at alternating intervals. With the invention, an absorbent headband apparatus is provided which does not include rupturable, pressurized, fluid filled cells. With the invention, an absorbent headband apparatus provides a specific absorbent layer, which is closest to the wearer's forehead, in which a midportion layer thickness is greater than the thickness at the ends of the specific absorbent layer. With the invention, an absorbent headband apparatus is provided in which the midportion height is greater than the end portion height.

Thus, while the present invention has been shown in the drawings and fully described above with particularity and detail in connection with what is presently deemed to be the most practical and preferred embodiment(s) of the invention, it will be apparent to those of ordinary skill in the art that many modifications thereof may be made without departing from the principles and concepts set forth herein, including, but not limited to, variations in size, materials, shape, form, function and manner of operation, assembly and use.

Hence, the proper scope of the present invention should be determined only by the broadest interpretation of the appended claims so as to encompass all such modifications as well as all relationships equivalent to those illustrated in the drawings and described in the specification.

Finally, it will be appreciated that the purpose of the annexed Abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. Accordingly, the Abstract is neither intended to define the invention or the application, which only is measured by the claims, nor is it intended to be limiting as to the scope of the invention in any way.

What is claimed as being new and desired to be protected by Letters Patent of the United States is as follows:

1. A headband apparatus, comprising:

a flexible, resilient C-shaped core member, said C-shaped core member defining a convex outer side and a concave inner side, a first absorbent layer attached to said core member, a cloth layer attached to said first absorbent layer, and a second absorbent layer interposed between said concave inner side of said C-shaped core member and said cloth layer, wherein said apparatus has a midportion and two end portions, wherein said midportion has a midportion thickness, wherein each of said two end portions has an end portion thickness, and wherein said midportion thickness is greater than said end portion thickness, whereby the thickness of said apparatus tapers from said midportion to said two end portions, wherein said first absorbent layer is comprised of a first foam material, and wherein said second absorbent layer is comprised of a loose second foam material.

2. The apparatus of claim 1 wherein said first absorbent layer jackets said core member.

3. The apparatus of claim 1 wherein said core member is comprised of a flexible, resilient plastic material.

4. The apparatus of claim 1 wherein said cloth layer jackets said first absorbent layer.

5. The apparatus of claim 1 wherein said cloth layer is comprised of terrycloth material.

6. The apparatus of claim 1 wherein:

said midportion has a midportion height, each of said two end portions has an end portion height, and said midportion height is greater than said end portion height, whereby the height of said apparatus tapers from said midportion to said two end portions.

7. The apparatus of claim 1 wherein:

said second absorbent layer includes a layer midportion which has a midportion layer thickness and includes two layer end portions which have an end layer thickness, and said midportion layer thickness is greater than said end layer thickness, whereby the thickness of said second absorbent layer tapers from said layer midportion to said layer end portions.

8. A headband apparatus, comprising:

a flexible, resilient C-shaped core member, said C-shaped core member defining a convex outer side and a concave inner side, a first absorbent layer attached to said core member, a cloth layer attached to said first absorbent layer, and a second absorbent layer interposed between said concave inner side of said C-shaped core member and said cloth layer, wherein said apparatus has a midportion and two end portions, wherein said midportion has a midportion thickness, wherein each of said two end portions has an end portion thickness, and wherein said midportion thickness is greater than said end portion thickness, whereby the thickness of said apparatus tapers from said midportion to said two end portions, wherein said midportion has a midportion height, wherein each of said two end portions has an end portion height, wherein said midportion height is greater than said end portion height, whereby the height of said apparatus tapers from said midportion to said two end portions, wherein said second absorbent layer includes a layer midportion which has a midportion layer thickness and includes two layer end portions which have an end layer thickness, and wherein said midportion layer thickness is greater than said end layer thickness, whereby the thickness of said second absorbent layer tapers from said layer midportion to said layer end portions.

* * * * *